(12) United States Patent
Duflos et al.

(10) Patent No.: US 6,686,378 B2
(45) Date of Patent: Feb. 3, 2004

(54) DERIVATIVES OF 3-IMINO-1,2-DITHIOLES, METHOD FOR PRODUCING THEM AND PHARMACEUTICAL COMPOSITIONS CONTAINING THE SAME

(75) Inventors: Muriel Duflos, Vue (FR); Jean-Michel Robert, Nantes (FR); Marie-Renée Nourrisson, La Chapelle sur Erore (FR); Guillaume Le Baut, Saint Sebastien sur Lore (FR); Daniel-Henri Caignard, Le Pecq (FR); Jean-Guy Bizot-Espiard, Paris (FR); Pierre Renard, Le Chesnay (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 10/168,875
(22) PCT Filed: Dec. 21, 2000
(86) PCT No.: PCT/FR00/03632
§ 371 (c)(1), (2), (4) Date: Jun. 21, 2002
(87) PCT Pub. No.: WO01/46180
PCT Pub. Date: Jun. 28, 2001

(65) Prior Publication Data
US 2003/0013742 A1 Jan. 16, 2003

(30) Foreign Application Priority Data
Dec. 22, 1999 (FR) .............................. 9916194

(51) Int. Cl.⁷ .................. A61K 31/4436; C07D 409/14
(52) U.S. Cl. ........................................ 514/333; 546/256
(58) Field of Search ........................... 546/256; 514/333

(56) References Cited

PUBLICATIONS

J.A. Mitchell, et al., "Studies of Heterocyclic Compounds, Part 28." J. Chem. Soc. Perkin Transactions 1., 1982;2:499–507.

Primary Examiner—Patricia L. Morris
(74) Attorney, Agent, or Firm—The Firm of Hueschen and Sage

(57) ABSTRACT

Compound of formula (I):

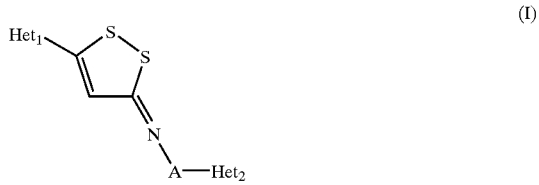

wherein:
  $Het_1$ and $Het_2$, which may be identical or different, each represents an optionally substituted pyridyl,
  A represents a bond or linear or branched ($C_1$–$C_6$) alkylene,
its optical isomers, where they exist, and addition salts thereof with a pharmaceutically acceptable acid.

4 Claims, No Drawings

DERIVATIVES OF 3-IMINO-1,2-DITHIOLES, METHOD FOR PRODUCING THEM AND PHARMACEUTICAL COMPOSITIONS CONTAINING THE SAME

The present invention relates to new 3-imino-1,2-dithiol compounds, to a process for their preparation, to pharmaceutical compositions containing them, and to their use as anti-inflammatories and, more especially, as anti-psoriatics.

To this date, the applicants know of no anti-inflammatory compound having a structure close to that of the products of the invention.

In addition to the fact that they are particularly novel, the products of the invention exhibit anti-inflammatory properties which are evident not only after administration by the systemic route, but also after topical administration, making them of particular interest for cutaneous disorders, such as, for example, psoriasis, acne or dermatites.

Psoriasis is a disorder of the skin that is characterised by a hyperproliferation of the keratinocytes of the epidermis. Its development is chronic, interrupted by remissions, and it is associated with inflammation.

Currently, the therapies used for this disorder (retinoids, arotinoids, glucocorticoids, vitamin D analogues, UVA irradiation) are only partially effective and have adverse effects.

There has therefore been particular interest in the synthesis of new compounds that are more active and at the same time devoid of toxicity.

The present invention relates more specifically to the compounds of formula (I):

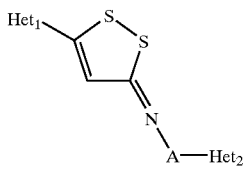

wherein:
  $Het_1$ and $Het_2$, which may be identical or different, each represents a heteroaryl group,
  A represents a bond or a linear or branched $(C_1-C_6)$ alkylene group,
to their optical isomers, where they exist, and to addition salts thereof with a pharmaceutically acceptable acid.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid.

A heteroaryl group is to be understood as meaning an aromatic mono- or bi-cyclic group having from 5 to 12 ring members containing one, two or three hetero atoms selected from oxygen, nitrogen and sulphur, wherein the heteroaryl group may optionally be substituted by one or more identical or different atoms or groups selected from the halogen atoms and the groups linear or branched $(C_1-C_6)$alkyl, hydroxy, linear or branched $(C_1-C_6)$alkoxy, linear or branched $(C_1-C_6)$polyhaloalkyl, nitro and amino (optionally substituted by one or more linear or branched $(C_1-C_6)$alkyl groups). Amongst the heteroaryl groups, the following groups may be mentioned, without implying any limitation: thienyl, pyridyl, furyl, pyrrolyl, imidazolyl, oxazolyl, isoxazolyl, thiazolyl, isothiazolyl, quinolyl, isoquinolyl, pyrimidinyl, benzimidazolyl.

The preferred $Het_1$ group of formula (I) is the optionally substituted pyridyl group.

The preferred $Het_2$ group of formula (I) is the optionally substituted pyridyl group.

The preferred compound of formula (I) is 3-(3-pyridyl)-5-[N-(4,6-dimethyl-2-pyridyl)-imino]-1,2-dithiol.

The invention extends also to a process for the preparation of the compounds of formula (I) which is characterised in that a compound of formula (II):

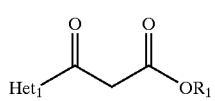

wherein $Het_1$ has the same meaning as in formula (I) and $R_1$ represents a linear or branched $(C_1-C_6)$alkyl group, is reacted
with a compound of formula (III):

wherein $Het_2$ and A have the same meanings as in formula (I),
to yield a compound of formula (IV):

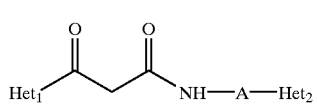

wherein $Het_1$, $Het_2$ and A have the same meanings as in formula (I),
which is reacted with a thionation agent to yield a compound of formula (I),
which is purified, if necessary, according to a conventional purification technique, and which is converted, if desired, into addition salts with a pharmaceutically acceptable acid.

The compound of formula (II) is obtained starting from a compound of formula (V):

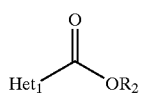

wherein $Het_1$ has the same meaning as in formula (I), and $R_2$ represents a linear or branched $(C_1-C_6)$alkyl group,
in accordance with the process described in J. Org. Chem. 1983, 48, 5007.

The invention extends also to a particular process for the preparation of 3-(3-pyridyl)-5-[N-(4,6-dimethyl-2-pyridyl)-imino]-1,2-dithiol, which is characterised in that a compound of formula (IIa), a particular case of the compounds of formula (II):

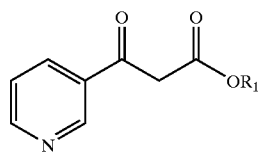

wherein $R_1$ has the same meaning as hereinbefore, is reacted with the compound of formula (IIa), a particular case of the compounds of formula (III):

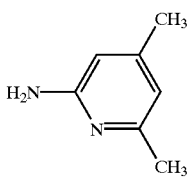

(IIIa)

to yield the compound of formula (IVa), a particular case of the compounds of formula (IV):

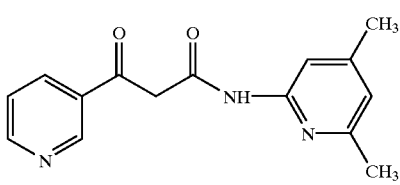

(IVa)

which is reacted with a thionation agent, such as, for example, Lawesson's reagent, to yield 3-(3-pyridyl)-5-[N-(4,6-dimethyl-2-pyridyl)-imino]-1,2-dithiol,
which is purified according to a conventional purification technique, and which is converted, if desired, into addition salts with a pharmaceutically acceptable acid.

N-(4,6-Dimethyl-2-pyridyl)-3-oxo-3-(3-pyridyl)-propionamide, compound of formula (IVa), is new and also forms part of the invention as an intermediate in the synthesis of 3-(3-pyridyl)-5-[N-(4,6-dimethyl-2-pyridyl)-imino]-1,2-dithiol.

In addition to the fact that they are new, the compounds of formula (I) have valuable pharmacological properties.

A study of the properties has, in fact, shown that the compounds of formula (I) are not toxic and that they possess an anti-inflammatory activity demonstrated just as well by the topical route as by the systemic route.

That spectrum of activity thus renders the compounds of the present invention useful in the treatment of chronic or acute arthritis and useful in a certain number of indications, such as inflammatory rheumatisms, rheumatoid polyarthritis, ankylosing spondylarthritis, arthroses, articular rheumatisms, and lumbagos. In view of their activity when administered topically, the compounds of the invention are useful in the treatment of some cutaneous disorders, such as, for example, psoriasis, acne and dermatites.

The present invention relates also to pharmaceutical compositions comprising a compound of formula (I), or an addition salt thereof with a pharmaceutically acceptable acid, in combination with one or more appropriate inert, non-toxic excipients.

Amongst the pharmaceutical compositions according to the invention there may be mentioned more especially, as examples and without implying any limitation, those which are suitable for oral, parenteral, nasal, rectal, perlingual, ocular, cutaneous, transcutaneous, percutaneous or pulmonary administration and, especially, injectable preparations, aerosols, eye or nose drops, suppositories, tablets, film-coated or sugar-coated, gelatin capsules, capsules, creams, ointments and dermal gels.

The useful dosage varies according to the age, sex and weight of the patient, the administration route, and the nature of the disorder and of any associated treatments the patient may be receiving, and ranges from 1 mg to 5 grams per 24 hours, preferably from 1 mg to 500 mg per 24 hours.

The following Examples illustrate the invention and do not limit it in any way.

The starting materials employed are known products or products prepared according to known preparation procedures.

Preparations A to D yield synthesis intermediates for use in the preparation of the compounds of the invention.

The structures of the compounds described in the Examples were determined according to customary spectrometric techniques (infra-red, NMR, mass spectrometry).

Preparation A

Methyl 3-oxo-3-(4-pyridyl)-propionate

The expected product is obtained in accordance with the process described in J. Org. Chem. 1983, 48, 5007 starting from methyl isonicotinate.

Preparation B

Methyl 3-oxo-3-(2-pyrazinyl)-propionate

The expected product is obtained in accordance with the process described in J. Org. Chem. 1983, 48, 5007 starting from methyl pyrazine-2-carboxylate.

Preparation C

Methyl 3-oxo-3-(5-methyl-2-thienyl)-propionate

The expected product is obtained in accordance with the process described in J. Org. Chem. 1983, 48, 5007 starting from methyl 5-methylthiophene-2-carboxylate.

Preparation D

Methyl 3-oxo-3-(2-furyl)-propionate

The expected product is obtained in accordance with the process described in J. Org. Chem. 1983, 48, 5007 starting from methyl furan-2-carboxylate.

EXAMPLE 1

3-(3-Pyridyl)-5-[N-(4,6-dimethyl-2-pyridyl)-imino]-1,2-dithiol

Step A: N-(4,6-Dimethyl-2-pyridyl)-3-oxo-3-(3-pyridyl)-propionamide

The expected product is obtained in accordance with the process described in J. Chem. Soc. (C) 1969, 89 starting from 2-amino-4,6-dimethylpyridine and from methyl 3-oxo-3-(3-pyridyl)-propionate described in J. Org. Chem. 1983, 48, 5007.

Step B: 3-(3-Pyridyl)-5-[N-(4,6-dimethyl-2-pyridyl)-imino]-1,2-dithiol 12 mmol of Lawesson's reagent are added at 120° C. to 10 mmol of the compound obtained in the preceding Step dissolved in toluene. After heating for 45 minutes, the toluene is evaporated off and the crude residue obtained is purified, first by chromatography on silica using as eluant ethyl ether and then a 98/2 methylene chloride/ethanol mixture, and then by crystallisation from isopropyl ether, to yield the expected product. Melting point: 152° C.

EXAMPLE 2

3-[3-Pyridyl]-5-[N-(5-methyl-1,3-thiazol-2-yl)-imino]-1,2-dithiol

The expected product is obtained in accordance with the procedure described in Example 1, starting from 2-amino- 5-methyl-1,3-thiazole and from methyl 3-oxo-3-(3-pyridyl)-propionate described in J. Org. Chem. 1983, 48, 5007.

EXAMPLE 3

3-(3-Pyridyl)-5-[N-(pyrimidin-2-yl)-imino]-1,2-dithiol

The expected product is obtained in accordance with the procedure described in Example 1, starting from 2-aminopyrimidine and from methyl 3-oxo-3-(3-pyridyl)-propionate described in J. Org. Chem. 1983, 48, 5007.

EXAMPLE 4

3-(4-Pyridyl)-5-[N-(5-chloro-2-pyridyl)-imino]-1,2-dithiol

The expected product is obtained in accordance with the procedure described in Example 1, starting from the compound described in Preparation A and 2-amino-5-chloropyridine.

EXAMPLE 5

3-(2-Pyrazinyl)-5-[N-(4-methoxy-6-methylpyrimidin-2-yl)-imino]-1,2-dithiol

The expected product is obtained in accordance with the procedure described in Example 1, starting from the compound described in Preparation B and 2-amino-4-methoxy-6-methyl-pyrimidine.

EXAMPLE 6

3-(5-Methyl-2-thienyl)-5-[N-(5-nitro-1,3-thiazol-2-yl)-imino]-1,2-dithiol

The expected product is obtained in accordance with the procedure described in Example 1, starting from the compound described in Preparation C and 2-amino-5-nitro-1,3-thiazole.

EXAMPLE 7

3-(2-Furyl)-5-[N-(2-pyrazinyl)-imino]-1,2-dithiol

The expected product is obtained in accordance with the procedure described in Example 1, starting from the compound described in Preparation D and 2-aminopyrazine.

EXAMPLE 8

3-(3-Pyridyl)-5-[N-((3-pyridyl)-methyl)-imino]-1,2-dithiol

The expected product is obtained in accordance with the procedure described in Example 1, starting from methyl 3-oxo-(3-pyridyl)-propionate described in J. Org. Chem. 1983, 48, 5007 and 3-picolylamine.

Pharmacological Study of the Compounds of the Invention

EXAMPLE 9

Demonstration of the Cutaneous (Topical) Anti-inflammatory Activity in an Acute Case Phorbol ester (phorbol 12-myristate 13-acetate) (5 μg) is applied topically to the front and rear surfaces of the right ear of the mouse 30 minutes after the application of the carrier (95% ethanol) or the agent. The difference in thickness between the right ear and the left ear (oedema) is measured 3 hours 30 minutes after the application of phorbol ester.

The percentage inhibition of cutaneous inflammation compared with a group of animals treated topically with 95% ethanol is calculated. The compounds of the invention enable an appreciable decrease in inflammation from a concentration of 30 μg/ear.

EXAMPLE 10

Demonstration of the Cutaneous (Topical) Anti-inflammatory Activity in a Curative Chronic Case (Psoriasis Model)

Phorbol ester (1 μg) is applied topically to the entire external surface of the right ear of the mouse on days 0, 2, 4, 7 and 9. The compounds to be studied or the carrier are applied topically twice per day at a dose of 2000 μg/10 μl per application on days 7, 8 and 9, and once only on the 10th day.

The difference in thickness between the right and left ears, which allows evaluation of the size of the cutaneous lesions and the extent of the inflammation, is measured on $D_0$, $D_2$, $D_4$, $D_7$ and $D_9$ 6 hours after the application of phorbol ester.

From the first day of application, the compounds of the invention enable an appreciable decrease in inflammation of more than 40% ($p<0.001$). The effect continues and becomes more pronounced right up to the end of the study, reaching a decrease in inflammation greater than 55% ($p<0.001$) on $D_{10}$.

Pharmaceutical Compositions

EXAMPLE 11

Tablets for the Treatment of Inflammatory Disorders

Formulation for the preparation of 1000 tablets each containing a dose of 10 mg

| | |
|---|---|
| compound of Example 1 | 10 g |
| hydroxypropyl cellulose | 2 g |
| wheat starch | 10 g |
| lactose | 100 g |
| magnesium stearate | 3 g |
| talc | 3 g |

EXAMPLE 12

Ointment Intended for the Treatment of Psoriasis

Formulation for the preparation of 100 kg of ointment containing a 1% dose

| | |
|---|---|
| Compound of Example 1 | 1000 g |
| Excipient in an amount sufficient for 100 kg: Ceatyl, stearyl, isopropyl alcohols; lanolin, polyethylene glycol monostearate, distilled water of cherry laurel | |

What is claimed is:

1. A compound selected from those of formula (I):

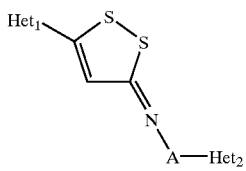

(I)

wherein:

Het$_1$ and Het$_2$, which may be identical or different, each represents an optionally substituted pyridyl, A represents a bond or linear or branched (C$_1$–C$_6$) alkylene, its optical isomers, where they exist, or addition salts thereof with a pharmaceutically acceptable acid, wherein optionally substituted is to be understood as meaning optionally substituted by one or more identical or different atoms or groups selected from halogen, linear or branched (C$_1$–C$_6$)alkyl, hydroxy, linear or branched (C$_1$–C$_6$) alkoxy, linear or branched (C$_1$–C$_6$)polyhaloalkyl, nitro and amino (optionally substituted by one or more linear or branched (C$_1$–C$_6$)alkyl).

2. A compound of claim 1, which is 3-(3-pyridyl)-5[N-(4,6-dimethyl-2-pyridyl)-imino]-1,2-dithiol, or its addition salts thereof with a pharmaceutically acceptable acid.

3. A method for treating a living animal body afflicted with a psoriasis, comprising the step of administering to the living animal body an amount of a compound of claim 1, which is effective for alleviation of said condition.

4. A pharmaceutical composition comprising as active principle an effective amount of a compound of claim 1, together with one or more pharmaceutically acceptable excipients or vehicles.

* * * * *

UNITED STATES PATENT AND TRADEMARK OFFICE
CERTIFICATE OF CORRECTION

PATENT NO. : 6,686,378 B2
DATED : February 3, 2004
INVENTOR(S) : Mauriel Duflos et al.

It is certified that error appears in the above-identified patent and that said Letters Patent is hereby corrected as shown below:

<u>Title page</u>,
Item [75], Inventors, "La Chapelle sur Erore" should be -- La Chapelle sur Erdre --; and "Saint Sebastien sur Lore" should be -- Saint Sebastien sur Loire --.

Signed and Sealed this

Twentieth Day of April, 2004

JON W. DUDAS
*Acting Director of the United States Patent and Trademark Office*